US00PP21374P2

(12) United States Plant Patent
Lyrene

(10) Patent No.: US PP21,374 P2
(45) Date of Patent: Oct. 12, 2010

(54) SOUTHERN HIGHBUSH BLUEBERRY PLANT NAMED 'FL05-627'

(50) Latin Name: ***Vaccinium corymbosum* L.**
Varietal Denomination: FL05-627

(75) Inventor: Paul M. Lyrene, Micanopy, FL (US)

(73) Assignee: Florida Foundation Seed Producers, Inc., Greenwood, FL (US)

( * ) Notice: Subject to any disclaimer, the term of this patent is extended or adjusted under 35 U.S.C. 154(b) by 0 days.

(21) Appl. No.: 12/584,555

(22) Filed: Sep. 8, 2009

(51) Int. Cl.
*A01H 5/00* (2006.01)

(52) U.S. Cl. ..... Plt./157

(58) Field of Classification Search ..... Plt./157
See application file for complete search history.

*Primary Examiner*—Susan B McCormick Ewoldt
(74) *Attorney, Agent, or Firm*—Jondle & Associates, P.C.

(57) ABSTRACT

'FL05-627' is a new southern highbush blueberry plant distinguished by a low chilling requirement with prolific early-spring leafing, a vigorous growth habit with a dense canopy, early ripening (50% ripe berries in north Florida by May 1) and very large and firm berries that have a medium to small picking scar, is disclosed.

3 Drawing Sheets

The present invention was supported in part by funds from the U.S. Government. The U.S. Government therefore may have certain rights in the invention.

Genus and species: *Vaccinium corymbosum* L.

Variety denomination: 'FL05-627'.

BACKGROUND OF THE INVENTION

The invention relates to a new and distinct variety of southern highbush blueberry (*Vaccinium corymbosum* L.) hybrid named 'FL05-627'. 'FL05-627' is intended for production of fresh-market blueberries in early spring from areas with mild winters and early spring warmth. 'FL05-627' is a southern highbush blueberry clone distinguished by its low chilling requirement and very large berries that ripen from mid-April to mid-May when grown in north Florida. Several hundred plants of 'FL05-627' have been propagated by softwood cuttings at Gainesville, Fla., and the resulting plants have all been phenotypically indistinguishable from the original plant.

'FL05-627' originated as a seedling from the cross of the proprietary *Vaccinium corymbosum* L. female parent, 'FL01-26' (unpatented) and the proprietary *Vaccinium corymbosum* L. male parent, 'Windsor' (U.S. Plant Pat. No. 12,783) as part of the University of Florida breeding program in a greenhouse at Gainesville, Fla. in February of 2001. The seedling was first fruited in a high-density field nursery in the spring of 2003. After the third year of fruiting in the field in the spring of 2005, 'FL05-627' was propagated by softwood cuttings in June of 2005, and an experimental 15-plant test plot was established as part of a variety test at Windsor, Fla. in January of 2006. Based on plant and berry characteristics of this plot, 'FL05-627' was selected for re-propagation by softwood cuttings in May of 2007, and an experimental 200-plant test plot was planted the following winter at Waldo in north Florida. Both the original and secondary plots were observed from flowering through fruit ripening in the spring of 2009, and no mutations or off-type plants have been observed.

'FL05-627' has been reproduced asexually for over eight years using softwood cuttings and has been found to retain its distinctive characteristics through successive asexual propagations.

Plant Breeder's Rights for this cultivar have not been applied for. 'FL05-627' has not been made publicly available more than one year prior to the filing date of this application.

SUMMARY OF THE INVENTION

The following are the most outstanding and distinguishing characteristics of 'FL05-627' when grown under normal horticultural practices in north Florida.

1. A low chilling requirement with prolific early-spring leafing;
2. A vigorous growth habit with a dense canopy;
3. Early ripening (50% ripe berries in north Florida by May 1); and
4. Very large and firm berries that have a medium to small picking scar.

DESCRIPTION OF THE PHOTOGRAPHS

This new southern highbush blueberry plant is illustrated by the accompanying photographs which show the plant's form, foliage, flower clusters and berry clusters. The colors shown are as true as can be reasonably obtained by conventional photographic procedures. The photograph of the flowers in FIG. 1 was taken in February of 2009. The photographs of the berries in FIG. 2 and FIG. 3 were taken in April of 2009. The photographs were taken using flowers and fruit from 3.5-year-old plants, growing under field conditions in north Florida.

DESCRIPTION OF THE NEW CULTIVAR

Figure 1:
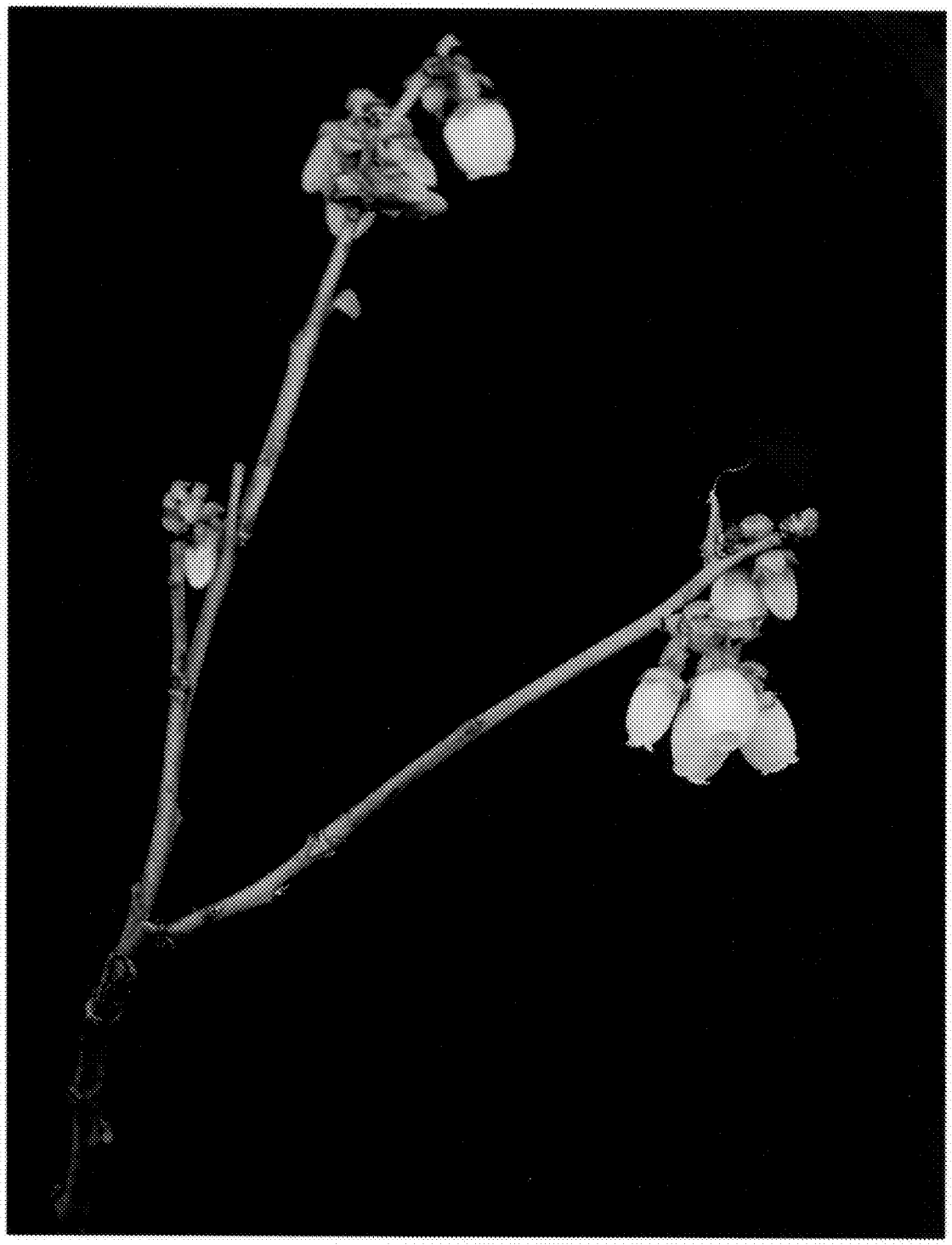
FIG. 1 shows a several clusters of opening flowers during the early stages of flowering in February. The flowers, which are urceolate to cylindrical in shape, are pinkish red before they open, especially in cold weather, becoming white by the time of anthesis.
Figure 2:
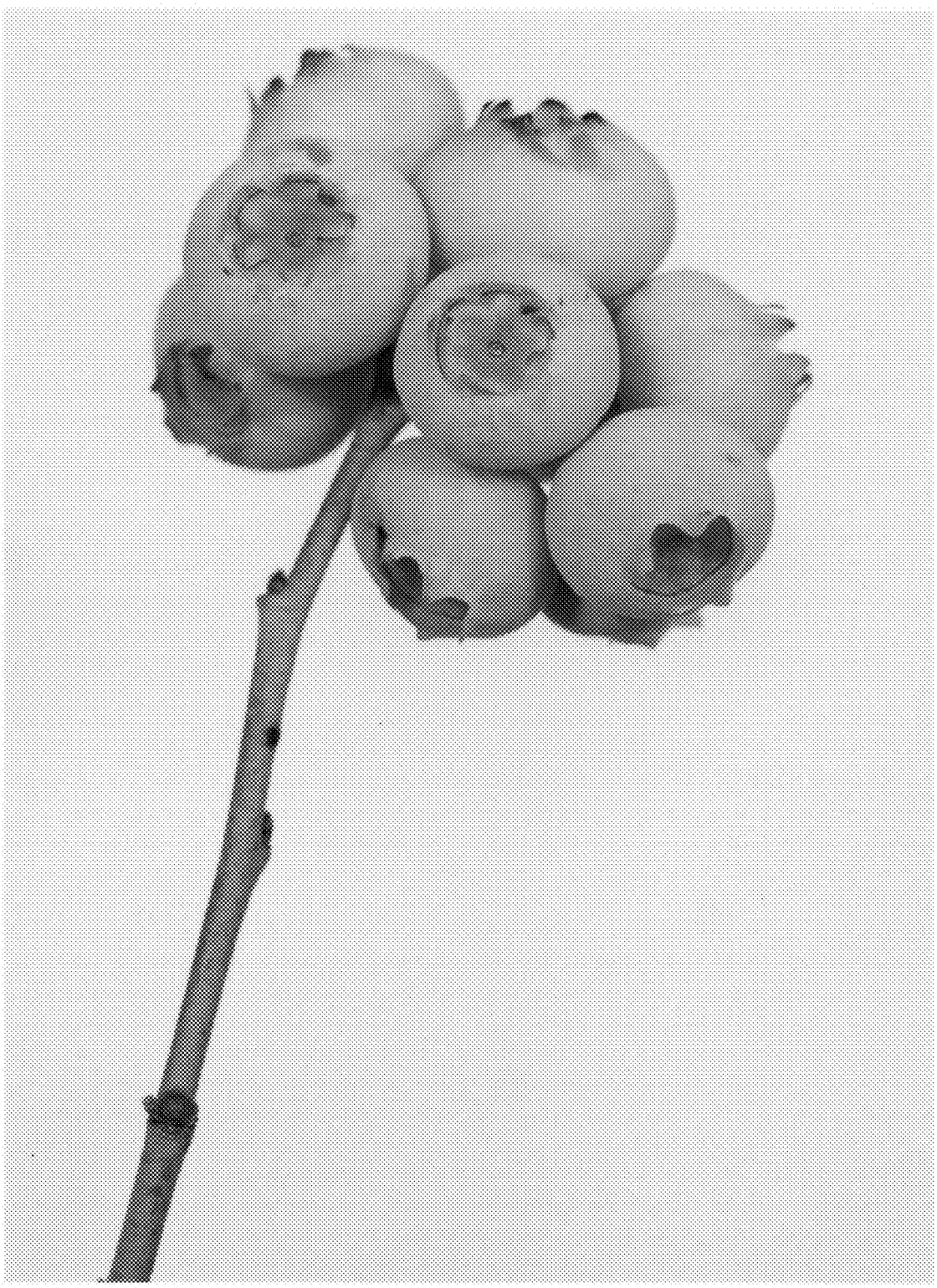
FIG. 2 shows a cluster of berries about a week before ripening, showing the wide, flat calyx aperture.
Figure 3:
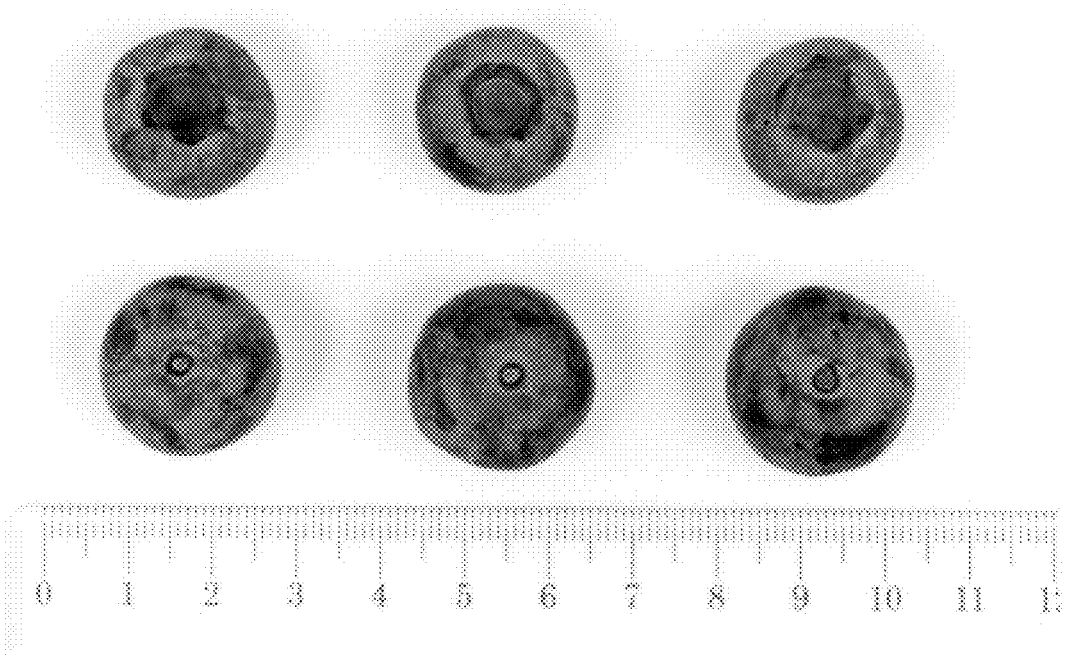
FIG. 3 shows berries at close range. The small, dry picking scar and relatively undeveloped calyx lobes are visible.

The following detailed description sets forth the distinctive characteristics of 'FL05-627'. The detailed description was taken on 3.5-year-old plants growing under field conditions near Windsor in northeast Florida. The color chart used in this specification is "The Pantone Book of Color", by Leatrice Eiseman and Lawrence Herbert. Harry N. Abrams, Inc., Publishers, N.Y. (1990). Where colors in the drawings differ from the Pantone color designations in the verbal descriptions, the Pantone color designations are accurate.

DETAILED BOTANICAL DESCRIPTION

Classification:

*Botanical name.*—*Vaccinium corymbosum* L.

*Common name.*—Southern highbush blueberry.

*Denomination.*—'FL05-627'.

Parentage:

*Female parent.*—'FL01-26' (unpatented).

*Male parent.*—'Windsor' (U.S. Plant Pat. No. 12,783).

Market class: 'FL05-627' produces southern highbush blueberries suitable for both the fresh and processed fruit markets.

Bush description:

*Plant height.*—1.5 m.

*Canopy diameter* (*measured at the widest part of the bush*).—2.0 m.

*Vigor.*—High.

*Growth habit.*—Somewhat spreading; produces a dense canopy.

*Twigginess.*—Low.

*Tendency toward evergreenness.*—Medium to high.

*Productivity.*—In northeast Florida, 'FL05-627' produces 5 to 8 pounds of berries per bush on plants 3 years old or older.

*Chilling requirement.*—300 hours below 7° C.

*Cold hardiness.*—Flowers and fruit are hardy to −3° C.; during winter dormancy, the plant is hardy to −15° C.

*Ease of propagation.*—Easy to propagate from softwood cuttings; the plants survive and grow well in nursery beds.

Trunks and branches:

*Suckering tendency.*—Medium to high; 4-year-old plants have an average of 7 major canes arising from near the base.

*Surface texture* (*of strong, 6-month-old shoots observed in June*).—Smooth.

*Surface texture* (*of 3-year-old and older wood*).—Rough due to exfoliation and production of vertical cracks.

*Color of 4-month-old twigs observed in June in the field.*—"Celery Green", Pantone 13-0532.

*Color of 3-year-old rough-textured canes.*—"Cameo Rose", Pantone 14-1310.

*Internode length on strong, upright shoots measured in June.*—Averages about 2.5 cm.

Leaves:

*Length, mean* (*including petiole, from tip of petiole to end of blade*).—6.3 cm.

*Width, mean* (*at widest point*).—3.0 cm.

*Shape.*—Ovate, terminating in a very short dew tip, 0.2 mm long, which is visible with a 15X microscope.

*Margin.*—Entire.

*Apex.*—Acute.

*Base.*—Acute.

*Color.*—Upper surface: "Fairway", Pantone 18-6320. Lower surface: "Cameo Green", Pantone 14-6312.

*Pubescence* (*on both the upper and lower surfaces*).—Absent.

*Pubescence on margins.*—Absent.

*Relative time of leafing versus flowering.*—In commercial fields in north Florida, where the variety is sprayed with hydrogen cyanamide in midwinter, the variety begins to produce new leaves at the time of full bloom.

Flower:

*Arrangement.*—Flowers are arranged alternately along a short, leafless, deciduous branch.

*Fragrance.*—Slight rose scent.

*Shape.*—Urceolate to cylindrical.

*Flowering period.*—Mean date of 50% open flowers in Windsor, Florida is February 9.

*Cluster habit.*—Loose.

*Median number of flowers per cluster.*—5.

*Petals.*—Fused into a corolla with 5 lobes.

*Pedicel.*—Length at time of anthesis: 0.5 cm. Color: "Red Violet", Pantone 17-1818 on the surfaces exposed to sunlight.

*Peduncle.*—Length at time of anthesis: Highly variable; median is 0.7 cm. Color: "Red Violet", Pantone 17-1818 on the surfaces exposed to sunlight.

*Calyx.*—Surface texture: Smooth. Color at anthesis: "Herbal Garden", Pantone 15-0336.

*Corolla.*—Length, mean (from pedicel attachment to corolla tip excluding the pedicel): 1.1 cm. Diameter of tube (at widest point): 0.7 cm. Aperture diameter: 0.4 cm. Surface texture: Smooth. Color at anthesis: White.

Reproductive organs:

*Style length* (*top of ovary to stigma tip*).—0.8 cm.

*Location of tip of stigma relative to lip of the corolla.*—The tip of the stigma is recessed about 0.1 cm from the tip of the corolla tube.

*Pollen.*—General: When the pollen is stained with 2% acetocarmine, the potential pollen fertility can be measured; 98% of the pollen tetrads stain well and appear to be well formed. Abundance of shed: High. Color of dried pollen: "Winter White", Pantone 11-0507.

Self-fruitfulness: Low to medium; planting in field configurations that promote cross pollination with other southern highbush clones is recommended for all southern highbush blueberries in Florida.

Fruit:

*Mean date of first commercial harvest* (*25% of berries ripe*).—April 20.

*Mean date of mid-harvest.*—April 28.

*Mean date of last harvest.*—May 10.

*Size and shape of calyx lobes on mature berry.*—The lobes are of medium size, forming a 5-point star on some of the berries.

*Pedicel length on ripe berry.*—Median is 0.5 cm.

*Peduncle length on ripe berry.*—Variable; median is 0.5 cm.

*Detachment force for ripe berries.*—Low.

*Number of berries per cluster.*—Median is 5.

Berry:

*Cluster habit.*—Loose to medium.

*Weight* (*on well-pruned plants*).—3.1 g per berry.

*Height.*—1.5 cm.

*Width.*—1.9 cm.

*Diameter of calyx aperture on mature berry* (*longest diameter*).—0.8 cm.

*Shape.*—Subglobose; somewhat flattened on the polar axis, being wider than it is tall.

*Surface color of immature berries, with bloom.*—"Frozen Dew", Pantone 13-0513.

*Surface color of mature berries while on the plant.*—"Lilac Gray", Pantone 14-3003.

*Surface color of ripe berry after polishing.*—Shiny black.

*Surface wax.*—Medium to slightly below normal in amount and in persistence during handling of the berry.

*Pedicel scar.*—Medium to small and dry.

*Firmness.*—High.

*Flavor.*—Medium levels of acid and sugar.

Texture.—Good; small seeds, thin skin.

Seeds:

*Color of dried seeds.*—"Aztec", Pantone 18-1130.

*Weight of well-developed dried seed.*—0.3 mg per seed.

*Length of well-developed dried seed.*—Mean is 0.2 cm.

Disease and insect resistance: 'FL05-627' has medium to high in vigor and has shown good bush survival in the field. The fungal leaf spots that are common on highbush blueberries grown in Florida are easily controlled by approved fungicides.

COMPARISON WITH PARENTAL LINES AND KNOWN CULTIVARS

'FL05-627' is distinguished from the proprietary *Vaccinium corymbosum* L. female parent, 'FL01-26' (unpatented) in that 'FL05-627' has a larger berry and later flowering than 'FL01-26'.

'FL05-627' is distinguished from the proprietary *Vaccinium corymbosum* L. male parent, 'Windsor' (U.S. Plant Pat. No. 12,783) in that 'FL05-627' has a smaller picking scar, with a skin less likely to tear during harvest, than 'Windsor'.

'FL05-627' is distinguished from the comparison commercial variety 'Star' (U.S. Plant Pat. No. 10,675) in that 'FL05-627' has larger berries and a more vigorous growth habit than 'Star'.

I claim:

1. A new and distinct cultivar of southern highbush blueberry plant as shown and described herein.

* * * * *